United States Patent [19]

Hauser et al.

[11] 4,226,247
[45] Oct. 7, 1980

[54] BIOLOGICAL ELECTRODE

[75] Inventors: Ray L. Hauser; John F. Harris, both of Boulder, Colo.

[73] Assignee: Hauser Laboratories, Boulder, Colo.

[21] Appl. No.: 935,480

[22] Filed: Aug. 21, 1978

[51] Int. Cl.³ .............................................. A61B 5/04
[52] U.S. Cl. ............................... 128/641; 128/303.13; 128/798
[58] Field of Search ................................ 128/639–641, 128/644, 783, 798, 802, 303.13

[56] References Cited

U.S. PATENT DOCUMENTS

| 1,975,518 | 10/1934 | Rose | 128/798 |
|---|---|---|---|
| 3,565,059 | 2/1971 | Hauser et al. | 128/640 |
| 3,812,861 | 5/1974 | Peters | 128/798 |
| 3,972,329 | 8/1976 | Kaufman | 128/641 |
| 3,993,049 | 11/1976 | Kater | 128/641 X |
| 4,004,578 | 1/1977 | Palmius | 128/640 |
| 4,066,078 | 1/1978 | Berg | 128/641 |
| 4,102,331 | 7/1978 | Grayzel et al. | 128/640 |

Primary Examiner—Lee S. Cohen

Attorney, Agent, or Firm—Sheridan, Ross, Fields & McIntosh

[57] ABSTRACT

A low-impedance biological electrode device for establishing electrical connection between the human body and electrical recording or stimulating apparatus without the use of conducting fluids, such as, gels, pastes and electrolytes, comprising, a substantially planar relatively thin electrode body, having as the electrically conducting connecting unit contacting the human body, a plurality of individual longitudinally extending strands, fibers, or filaments of conducting material embedded in a pressure-sensitive or solvent-activated adhesive which serves to bond the strands together in a composite connecting unit and to bond the connecting unit on one side to said electrode body and on the other side or interface to the human body, a modification being the use of strands cross-oriented with respect to the longitudinal strands, as exemplified by woven conductive material, the connecting unit being provided with a transverse bus bar in the form of metal foil in electrical contact with an electrical connecting element for conducting current from the connecting unit in contact with the human body to the electrical recording or stimulating apparatus.

4 Claims, 6 Drawing Figures

BIOLOGICAL ELECTRODE

BACKGROUND OF THE INVENTION

1. Field of the Invention

Electro-medical electrodes for establishing electrical connection between an animal body, specifically the human body, and an electrical recording device.

2. Description of the Prior Art

In the prior medical art it has been a well known practice to attach electrodes to the skin to provide contact and through which electrical signals are transmitted between the anatomy and electromedical apparatus. U.S. Pat. to Baum, No. 3,187,745 and Berman, No. 3,085,577 are exemplary of such electrodes, employed in the art of electrocardiography wherein electrical heart signals are received, and the U.S. Pat. to Alderman, No. 2,872,926, is exemplary of an electrode employed in the art of electroencephalography wherein electrical brain signals are received. The signals, in either event, are suitably recorded or charted and are a measure of a body function or functions under known conditions, such as rest, exercise, mental stress, intensive care and the like. Also, with the advent of space travel and radio monitoring, or with the use of small portable electromedical recording devices, it is now possible to biologically monitor body functions of pilots under conditions encountered in fulfilling their missions. The importance of maintaining a low resistance contact with the anatomy is well recognized and the patents referred to are exemplary of obtaining the desired results by utilizing electrolytes, electroconductive gels, pastes and/or adhesives through which an electric signal is transmitted. Other pertinent U.S. Pat. Nos. are 2,555,037; 2,985,172; 3,170,459; 3,474,775; 3,475,213; 3,565,059; 3,607,788; 3,710,782; 3,713,435; and 3,911,906. The U.S. Pat. to Howell, No. 2,943,628 is exemplary of another approach wherein contact is made with metal foil surrounded by a pressure sensitive adhesive.

As the art referred to has advanced, certain improvements appear desirable, including the need for more rapid and expedient application of the electrodes and simplification of their construction, together with its attendant reduction of cost. Additionally, a light weight electrode is desirable to minimize or obviate inertial movement relative to a predetermined position on the skin.

Prior art biological electrodes for electrocardiography are not capable of rapid attachment to the body and rapid removal therefrom, are not non-irritating, transparent to medical x-rays, or easily removed by dissolution of adhesive or by peeling. The adhesive used with prior art biological electrodes, such as gelled pads, has a tendency to dry out during storage or use, and in some cases serves as a nutrient for bacteria.

While others have taught the incorporation of conducting particles into electrode surfaces, the absence from their teaching of several critical elements prevented them from disclosing products of practical utility. A satisfactory biological electrode must exhibit at least two required properties; (1) it must provide a high electrical conductivity through the skin, and (2) it must have enough adhesive strength to remain securely in place on the patient. It has been found that the use of particles of conventional geometry, i.e., "fine powder carbon" (Reinhold U.S. Pat. No. 3,911,906), silver flakes or their metal particles (Burton U.S. Pat. No. 4,008,721), and carbon black (Johnson U.S. Pat. No. 3,474,775), results in pressure sensitive electrodes which may have one, but never both of the above properties. Prior electrodes having satisfactory conductivity did not have enough adhesive strength, and increasing the adhesive content to cure this defect resulted in lowering the conductivity to an unsatisfactory level.

Stow U.S. Pat. No. (3,475,213) overcome part of the problem with the use of particles having a "substantial thickness in relation to their width and length", typically "spheres or granules". While solving part of the problem, particles of this geometry still leave conductivity across the face of the electrode so low as to require a conductive backing material. This backing material would typically be a metal foil, and would not lend itself well to the skin "breathability" or conformability desirable in a biological electrode.

The present invention, which is described hereinafter, takes advantage of the unique geometry of fibers used with a "soft" (deformable on a microscopic scale) adhesive to solve the problems not addressed by the prior art. In contrast to the particles used by Stow, fibers have a high length-to-thickness (diameter) ratio, and thus a single fiber may make physical and electrical contact with the many other fibers that may cross it anywhere along its length. This property of fibers provides a very high conductivity at low fiber concentrations in the adhesive, thus permitting the construction of an electrode having good adhesive strength, good electrical properties, and no foil backing. The particles mentioned in the prior art, on the other hand, can make contact with only a few other particles, and then only in the confines of a non-linear geometry, resulting in the limitations already discussed.

For use as a biological electrode, conductivity through the electrode is important, but is not enough in itself; the electrode surface must provide for high conductivity to the skin and into the body. Fibers imbedded in a rigid or semirigid binder might have excellent electrical properties throughout the electrode, but would not be able to provide the many necessary skin contacts to make a usable biological electrode interface. To facilitate good contact between the skin and fibers, the adhesive or binder in the electrode must be soft enough at the time of application to allow the adhesive to "flow" out of the way of the fibers, permitting as many fibers as possible to make direct contact with the skin. The adhesive then fills in any available voids provided by skin and fiber irregularities to provide for firm holding strength. The result is a series of microscopic hills (fibers) for conductivity, with adhesive in the valleys for holding strength. Thus the combination of fibers and the required type adhesive is important.

The above desired properties for the electrode of the present invention are obtained in one of two ways: (1) combining fibers with a soft, pressure sensitive adhesive, or (2) combining fibers with a solvent activated adhesive that is soft upon application to the skin, but becomes more rigid upon drying. For optimum properties, the fibers should have a very small diameter ($\approx 0.0003''$) and as high a length to diameter ratio as possible (preferably greater than 1500) for the following reasons. The small diameter of a fiber allows for more fibers per unit area of electrode surface, and thus better electrical properties. The greater the length of the fibers involved, the fewer fiber ends will be present on the electrode surface, resulting in less skin irritation to the patient. Unacceptable skin irritations and itching has been observed when 0.0003" diameter fibers are used in lengths much shorter than one-half inch, but very little irritation when longer fibers are used. Accordingly, fibers less than 0.0003" in diameter and at least one-half inch in length are preferred.

SUMMARY OF THE INVENTION

A low-impedance biological electrode device for establishing electrical connection between the human body and electrical recording or stimulating apparatus without the use of conducting fluids, such as, gels, pastes and electrolytes, comprising, a substantially planar relatively thin electrode body, having as the electrically conducting connecting unit contacting the human body, a plurality of individual longitudinally extending strands, fibers, or filaments of conducting material embedded in a pressure-senstive or solvent-activated adhesive which serves to bond the strands together in a composite connecting unit and to bond the connecting unit on one side to said electrode body and on the other side or interface to he human body, a modification being the use of strands cross-oriented with respect to the longitudinal strands, as exemplified by woven conductive material, the connecting unit being provided with a transverse bus bar in the form of a metal foil in electrical contact with an electrical connecting element for conducting current from the connecting unit in contact with the human body to the electrical apparatus.

The electrode is of laminated construction with the conducting connection unit having its interface which contacts the body covered with a plastic release cover which itself may be covered with a paper backing. A bus bar in the form of aluminum foil is adhesevely secured across one end of the conducting unit. A plastic strip is provided between the foil and the outer release strip. An electrical connecting plug is secured to the body to connect the foil to the appropriate electrical instrument. The strands of the conducting unit may be provided with an adhesive supporting backing. A gauze strip may be secured to the backing or to the fibers themselves and a final lamination of sponge rubber constitutes the other face of the electrode body. A preferred adhesive for securing the strands of the conducting unit together is plasticized polyvinylpyrrolidone.

DESCRIPTION OF THE PREFERRED EMBODIMENTS

The invention will now be described with reference to the accompanying drawing in which like numbers represent the parts.

Figure 1:
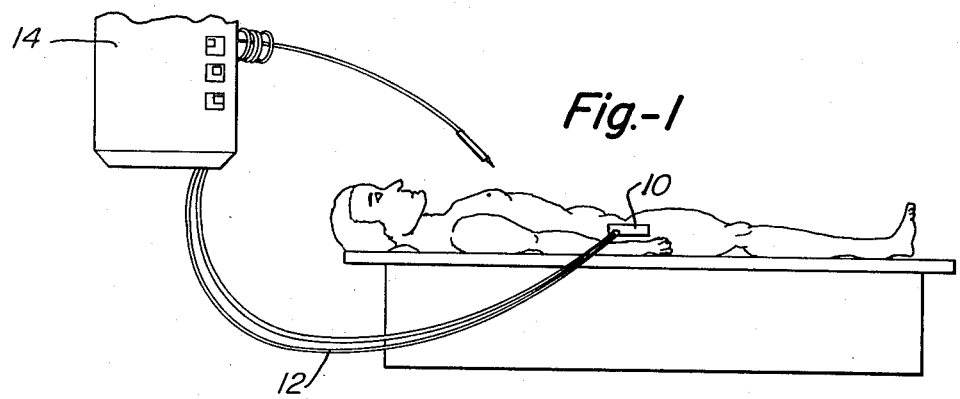
FIG. 1 is a diagrammatic showing of the electrode of the invention attached to the patient showing connections.

Referring to FIG. 1, the numeral 10 represents the electrode of the invention attached to the patient and connected by electrical connections 12 to an electrical instrument 14, such as an electrosurgery device.

Figure 2:
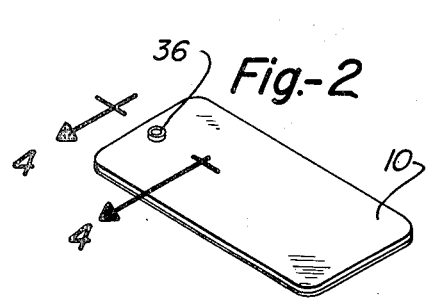
FIG. 2 is a plan view, partially in perspective, of the electrode of the invention.

Referring to FIG. 2, the electrode 10 is shown as a substantially planar, relatively thin structure, having an electrical connector 36 mounted in one end thereof.

Figure 3:
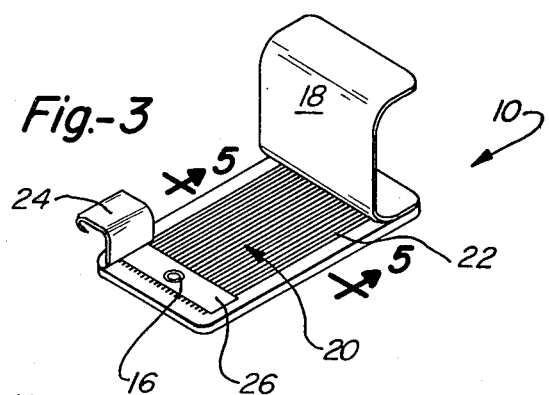
FIG. 3 is a plan view, partially in perspective, of the electrode, showing the release layer peeled back to expose the interface and showing the plastic strip covering the bus bar peeled back.

Referring to FIG. 3, the outer release strip 18 of suitable plastic is shown peeled back to expose the conducting connection unit indicated generally at 20. The release strip protects the adhesive surface of unit 20 until the electrode is ready for use. The connecting unit 20 is comprised of individual strands, fibers, or filaments 22, the majority of which are supported in a substantially planar orientation. These fibers or strands extend longitudinally over or through the length of the electrode body 10. The terms "over" and "through" mean that the fibers are supported throughout the unit including on its surface. Preferably, some of the fibers extend the entire length of the unit to provide a large area of coverage over the skin, although it is not required that any of the fibers do this. The fibrous strands or filaments are preferably made of graphite, such as, carbon yarn or other carbonized fiber, although they may be metallic fibers, knits and woven screens. The terms "fibers", "strands" and "filaments" are used interchangeably herein. If woven metallic or graphite screens are used, they will include fibers oriented transversely of the longitudinal fibers and they are referred to herein as being "cross-oriented", this term including any angular orientation of the transverse fibers with the longitudinal fibers. The fibers are secured together by a pressure sensitive or agent-activated adhesive, which forms the fibers into a composite units and serves to bind them on one side to the electrode and on the other side to the human body. By "agent-activated adhesive" is meant a composition which is made adhesive by means of an additive, such as, a solvent or one causing a chemical reaction. The adhesive must be sufficiently soft so that upon application of the electrode it will spread or "flow" away from the fibers or strands near the surface of the unit 20 to permit direct contact of the strands or fibers with the skin when the adhesive "sets", as the adhesives used are not conductive and one purpose of the invention is to avoid the use of conductive adhesives and like materials. The adhesive then fills in any voids between skin and fibers, including those formed by fiber and skin irregularities, to provide for firm holding strength. The resulting bond comprises a series of exposed microscopic hills (fibers) for conductivity, and valleys filled with adhesive for holding strength. The result is produced by the critical combination of properly planar oriented fibers and adhesive. The covering strip or insulator 24 of suitable plastic for the bus bar 26 is shown peeled back to expose the bus bar overlying one end of the conductive filaments 22 of connecting unit 20 and in electrical connection with a plug 16. In the preferred construction an aluminum foil 26 is used for the bus bar and is positioned transversely entirely across one end of the connecting unit 20 in electrical contact therewith.

Figure 4:
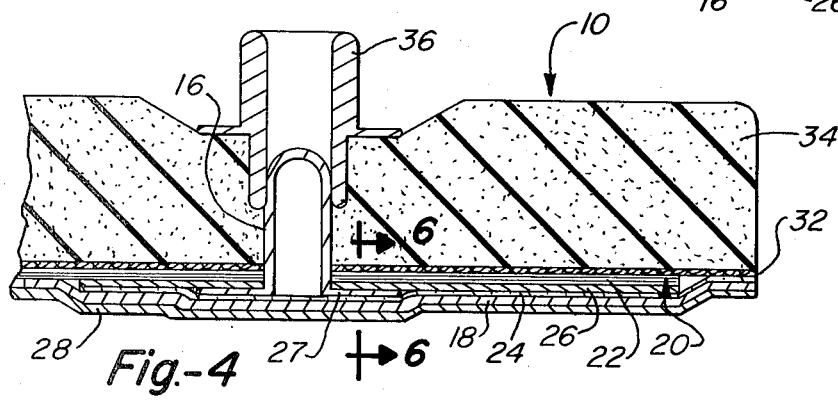
FIG. 4 is a cross section taken on line 4—4 of FIG. 2 showing an electrical receptacle attached to the plug which contacts the interface.
Figure 5:
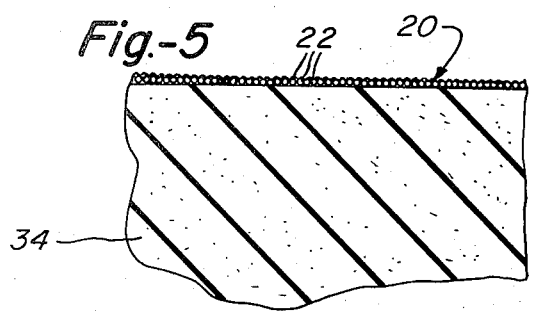
FIG. 5 is a fragmentary partial cross section of the interface and release layer.
Figure 6:
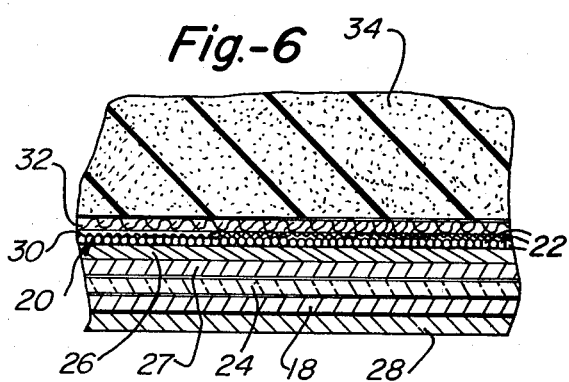
FIG. 6 is a fragmentary cross section taken on the line 6—6 of FIG. 4.

Referring to FIGS. 4, 5 and 6, the laminated structure of the electrode will now be described starting with the centrally located connecting unit 20 and proceeding in each direction. Proceeding toward the bottom of the electrode, the next layer as shown in the figures is the bus bar 26 over which is centrally positioned the circular flange constituting the base 27 of the electrical plug 16. The next succeeding layer is the plastic strip or cover 24 for protecting the bus bar 26 extending only far enough longitudinally of the connecting unit to perform this function. The final layer constituting the bottom of the electrode and covering the adhesive interface of the electrode and the cover 24 is the release strip 18.

An outer protective backing 28 of paper may be provided to protect the entire laminated structure. Proceeding in the other direction from the connecting unit 20, the conductive filaments 22 which are clearly illustrated in FIGS. 5 and 6 as being contiguous may be reinforced with an upper backing layer of adhesive covering 30. To this covering, or to the strands if no covering is used, a layer 32 of ordinary surgical gauze may be secured by a suitable adhesive for extra strength. An outer top covering 34, preferably of sponge rubber, is adhesively secured over the gauze layer to complete the laminated electrode structure.

An electrical connector 36 is provided for electrical connection to the electrical plug 16 as shown in FIGS. 2 and 4. Connector 36 is used to connect the plug 16, and in turn the connecting unit 20, with apparatus 14.

The pressure-sensitive or solvent-activated tacky adhesive used to bind the conducting filaments 22 together into a composite unit is an important feature of the invention as explained above. The preferred active ingredient of the adhesive is polyvinylpyrrolidone sold commercially under the trade name "PLASDONE K29-32". Other materials which may be used are a nitrocellulose base material sold commercially as "DUCO 5458", siloxane, vinyl acetate, acrylate, or other such type organic polymer. The adhesive mixture is compounded by mixing with the active agent a plasticizer such as dioctyl phthalate, camphor, glycerin, or other equivalent plasticizer and, alternatively, a conventional tackifier, such as, "IGEPAL CO-210". A suitable solvent for the solvent-activated adhesive is alcohol. Other conventional solvents may be used. The polyvinylpyrrolidone base adhesive can be formulated as a solvent activated or a pressure sensitive adhesive, and this is the preferred type adhesive for forming the adhesive matrix of strands and adhesive having the property of spreading or "flowing" upon application of unit 20 to permit direct contact of the fibers or strands with the skin. Other adhesive compositions may be used, such as some of those disclosed in the above-cited patents.

The adhesives serve not only to bond the conductive strands into a composite unit, but they also serve to bond the connecting unit 20 on one side into the electrode and to bond the unit 20 on its other side to the human body when applied thereto after removal of release strip 18.

The composition of the pressure sensitive organic adhesive or the solvent-activated adhesive can vary within fairly wide limits to provide an adhesive having the desired properties to permit maximum contact between conducting fibers and the skin, as discussed above. The conductive fibers in the composite electrical connecting unit 20 comprise about 10-90 percent by volume and preferably 40-50 percent by volume of the unit. The adhesive should have a cone penetration range of 0.5-10 cm. as determined by the ASTM test procedure D-217. The bond strength of the adhesive should range from 0.25-10 lb/inch as tested against stainless steel by ASTM test method D-903, the preferred range being 0.5-2.5 lb/inch width. The surface resistivity of the conductor/adhesive composite should be in the range of less than five ohms/sq. cm. Also the bus bar 26 should extend transversely of the consolidated strands and should extend entirely across the strands for the most effective transfer of electrical current.

In operation, the body area to which the electrode is to be applied is properly cleaned. The release strip 18 is then peeled off and if a pressure sensitive adhesive is used the electrode is applied to the arm or other body area by contacting the body area with the adhesively coated strands and applying pressure. If a solvent-activated adhesive is used, an activating solvent, such as alcohol, is applied to the adhesive before applying it to the body area. The receptacle 36 leading to the electrical recording instrument 14 is then inserted over the plug 16 and recordings noted.

Comparative tests were made with the electrode of the invention incorporating the novel conducting connecting unit 20 and with conventional electrodes using conducting gels and electrolytes, and the results are set forth in the following examples:

EXAMPLE 1

An electrode was prepared by placing graphite yarns in parallel, unidirectional, substantially planar orientation on an aluminum foil strip to serve as a bus bar, followed by impregnating the layup with a presure sensitive adhesive having the following composition:

| | |
|---|---|
| Polyvinylpyrrolidone (PLASDONE K 29-32) | 10 grams |
| Tackifier (IGEPAL CO-120) | 15 grams |
| Solvent (Denatured alcohol) | 15 grams |

The wet fibers were covered with a polyethelene film so that the composite could be rolled to compress the assembly. The polyethelene was removed, adhesive was dried, and electrical attachment was made by applying sufficient pressure of the contacting surface against the skin to insure that the adhesive "flowed" or spread away from the surface fibers to permit their direct contact with the skin. The adhesive then fills in any voids between skin and fibers, including those formed by fiber and skin irregularities, to provide for firm holding strength. The electrode was evaluated by placement on the right upper arm of a patient using its adhesive for attachment. For comparative purposes, a commercial dispersive electrode with pre-gelled electrolyte was placed in a comparable location on the left arm of the patient. Electrosurgical power was applied across the pair of electrodes. In the range of 130-150 watts the gelled electrode caused considerable stimulative sensation and some heating. In contrast, the conductive adhesive electrode of the invention produced no stimulation with a comparable amount of heating.

EXAMPLE 2

An electrode was prepared as in Example 1, except that the aluminum foil was used only in the form of a narrow strip perpendicular to the direction of the graphite fibers at the end where the electrical connector was attached. This pressure-sensitive electrode was applied and tested by the same tests used in Example 1 to 150 watts of electrosurgical coagulation power without adverse patient reaction. In contrast, the gelled electrode caused reaction at 135 watts.

Other successful tests giving comparable results to those of Examples 1 and 2, were made using metallic fibers, and knits and woven screens of metallic fibers and graphite fibers. Successful tests were also made using an electrode incorporating the conductive connecting unit 20 having conducting fibers impregnated with solvent activated adhesives in which the active agent was vinyl acetate, acrylate or other equivalent type organic polymers. Others which are operative are nitrocellulose and siloxane.

It was found that the electrodes as described above, using the operative combination of fibers and adhesive, and particularly those using the polyvinylpyrrolidone adhesive combination with the fibers, strands or filaments, were easily attached and removed and conformed accurately with the human body. As the Examples show, more efficient power dissipation without pain or heat development than with conventional electrosurgery pads using gels and electrolytes was obtained. It was found that the adhesive did not dry out during storage or during use. It was also found that the adhesive was not a nutrient for bacteria. The adhesive contained in the connecting unit 20 was non-irritating and the electrode was found to be transparent to medical x-rays. The impedance of the electrode was comparable to that of conventional electrodes using conductive gels, pastes, and electrolytes.

What is claimed is:

1. A biological electrode for electrically connecting the skin of the human body to an electrical recording or stimulating device, said electrode comprising:

a plurality of longitudinally extending contiguous strands of conducting material, all of said strands lying generally parallel to each other, said strands having first and second opposed surfaces;

a thin layer of sponge rubber attached to said first surface of said strands to maintain them in adjacent parallel relationship;

a bus bar extending across one end of said second surface of said strands and in electrical contact therewith;

an adhesive coated over the remainder of said second surface of said strands to form a conductor/adhesive composite wherein said strands are imbedded in said adhesive, said adhesive being displacable from said strands as said electrode is pressurally applied to the skin so that said second surface of each of said strands contacts the skin substantially along its entire length and said adhesive fills any voids formed by skin and strand irregularities so that said electrode is adhered to the skin in all areas not contacted by said strands; and an electrical plug connected to said bus bar and extending through said layer of sponge rubber for connection to the electrical recording or stimulating device.

2. The biological electrode of claim 1 in which said adhesive has a cone penetration range of about 0.5–10 cm., and a bond strength between about 1.5–2.5 lb./inch width, and said conductor/adhesive composite has a surface resistivity of less than 5 ohms/sq. cm.

3. The biological electrode of claim 1 in which conductive strands comprise about 10–90 percent by volume of the electrode.

4. The biological electrode of claim 3 in which said conducting strands have a diameter not substantially in excess of about 0.0005" and a length to diameter ratio not substantially less than about 1500.

* * * * *